(12) United States Patent
Melnik

(10) Patent No.: US 9,981,158 B2
(45) Date of Patent: May 29, 2018

(54) ACTIVE FITNESS CHAIR APPLICATION

(71) Applicant: Irina L Melnik, San Francisco, CA (US)

(72) Inventor: Irina L Melnik, San Francisco, CA (US)

( * ) Notice: Subject to any disclaimer, the term of this patent is extended or adjusted under 35 U.S.C. 154(b) by 2 days.

(21) Appl. No.: 15/155,058

(22) Filed: May 15, 2016

(65) Prior Publication Data

US 2016/0332028 A1 Nov. 17, 2016

Related U.S. Application Data

(60) Provisional application No. 62/336,722, filed on May 15, 2016, provisional application No. 62/162,317, filed on May 15, 2015.

(51) Int. Cl.
*A47C 31/12* (2006.01)
*A47C 9/00* (2006.01)
(Continued)

(52) U.S. Cl.
CPC .......... *A63B 24/0087* (2013.01); *A47C 9/002* (2013.01); *A47C 31/126* (2013.01);
(Continued)

(58) Field of Classification Search
CPC .............. A47C 9/002; A63B 21/00058; A63B 21/00069; A63B 21/00072; A63B 21/00076; A63B 21/00178; A63B 21/00181; A63B 21/00185; A63B 21/00192; A63B 21/002; A63B 21/0023; A63B 21/005; A63B 21/0051; A63B 21/0052; A63B 21/0058; A63B 21/0059; A63B 21/008; A63B 21/0083; A63B 21/0084; A63B 21/00845; A63B 21/0085; A63B 21/0087; A63B 21/0088; A63B 21/02; A63B 21/023; A63B 21/025; A63B 21/026; A63B 21/04; A63B 21/0407; A63B 21/0414; A63B 21/0421; A63B 21/0428; A63B 21/0435; A63B 21/0442; A63B 21/045; A63B 21/0455; A63B 21/05; A63B 21/0055; A63B 21/0555; A63B 21/0557; A63B 21/068; A63B 21/15; A63B 21/151; A63B 21/152; A63B 21/153;

(Continued)

(56) References Cited

U.S. PATENT DOCUMENTS 5,570,301 A * 10/1996 Barrus ................ A61B 5/103
702/150
5,776,084 A * 7/1998 Wolan ................ A61H 1/0292
482/111

(Continued)

*Primary Examiner* — Andrew S Lo
*Assistant Examiner* — Gary D Urbiel Goldner

(57) ABSTRACT

In one aspect, a computerized method includes the step of providing a dynamic exercise chair. The dynamic exercise chair includes a plurality of force providing elements that provide a resistance force to a seatback of the dynamic exercise chair. The dynamic exercise chair includes a plurality of position sensors that monitor a seatback position of the dynamic exercise chair. The dynamic exercise chair includes a microcomputer system that provides a set of control signals to the plurality of force providing elements, and receives a sensor data from the plurality of position sensors.

14 Claims, 6 Drawing Sheets

(51) Int. Cl.
| | |
|---|---|
| *A61B 5/00* | (2006.01) |
| *A63B 21/00* | (2006.01) |
| *A63B 21/002* | (2006.01) |
| *A63B 21/005* | (2006.01) |
| *A63B 23/02* | (2006.01) |
| *A63B 24/00* | (2006.01) |
| *A63B 71/06* | (2006.01) |
| *G06Q 10/06* | (2012.01) |

(52) U.S. Cl.
CPC ...... *A63B 21/005* (2013.01); *A63B 21/00069* (2013.01); *A63B 21/154* (2013.01); *A63B 21/4047* (2015.10); *A63B 23/0211* (2013.01); *A63B 23/0233* (2013.01); *A63B 71/0622* (2013.01); *G06Q 10/0639* (2013.01); *A61B 5/6891* (2013.01); *A63B 21/0023* (2013.01); *A63B 21/00072* (2013.01); *A63B 2024/0093* (2013.01); *A63B 2071/065* (2013.01); *A63B 2071/0625* (2013.01); *A63B 2071/0655* (2013.01); *A63B 2208/0233* (2013.01); *A63B 2213/004* (2013.01); *A63B 2220/10* (2013.01); *A63B 2220/16* (2013.01); *A63B 2220/30* (2013.01); *A63B 2220/34* (2013.01); *A63B 2220/40* (2013.01); *A63B 2220/44* (2013.01); *A63B 2225/093* (2013.01); *A63B 2225/20* (2013.01); *A63B 2225/50* (2013.01); *A63B 2230/06* (2013.01); *A63B 2230/30* (2013.01); *A63B 2230/40* (2013.01); *A63B 2230/50* (2013.01); *A63B 2230/60* (2013.01); *A63B 2230/62* (2013.01); *A63B 2230/65* (2013.01)

(58) Field of Classification Search
CPC ... A63B 21/154; A63B 21/158; A63B 21/159; A63B 21/16; A63B 21/1609; A63B 21/4027; A63B 21/4039; A63B 21/4031; A63B 21/4033; A63B 21/4034; A63B 21/4035; A63B 21/4041; A63B 21/4045; A63B 21/4047; A63B 21/4049; A63B 2023/006; A63B 23/02; A63B 23/0205; A63B 23/0211; A63B 23/0222; A63B 23/0233; A63B 23/0238; A63B 24/0003; A63B 24/0006; A63B 24/021; A63B 24/0059; A63B 24/0062; A63B 24/0087; A63B 2024/0009; A63B 2024/0012; A63B 2024/0025; A63B 2024/0065; A63B 2024/0068; A63B 2024/0071; A63B 2024/009; A63B 2024/0093; A63B 2024/0096; A63B 69/0057; A63B 69/0059; A63B 71/0054; A63B 71/0619; A63B 71/0622; A63B 2071/0072; A63B 2071/0647; A63B 2071/065; A63B 2071/0652; A63B 2071/0655; A63B 2071/0694; A63B 2208/02; A63B 2208/0228; A63B 2208/0233; A63B 2213/004; A63B 2220/10; A63B 2220/13; A63B 2220/16; A63B 2220/17; A63B 2220/30; A63B 2220/34; A63B 2220/40; A63B 2220/44; A63B 2220/50; A63B 2220/51; A63B 2220/52; A63B 2220/54; A63B 2220/56; A63B 2220/62; A63B 2220/64; A63B 2220/80; A63B 2220/803; A63B 2220/805; A63B 2225/09; A63B 2225/093; A63B 2225/20; A63B 2225/50; A63B 2030/06; A63B 2030/08; A63B 2030/30; A63B 2030/40; A63B 2030/50; A63B 2030/60; A63B 2030/62; A63B 2030/65; A63B 2030/75

See application file for complete search history.

(56) References Cited

U.S. PATENT DOCUMENTS

| | | | | |
|---|---|---|---|---|
| 7,163,263 | B1* | 1/2007 | Kurrasch | A47C 1/0242 297/217.3 |
| 8,596,716 | B1* | 12/2013 | Caruso | A47C 31/126 297/217.1 |
| 2002/0167486 | A1* | 11/2002 | Tan | B60N 2/002 345/156 |
| 2003/0073552 | A1* | 4/2003 | Knight | A47C 7/024 482/148 |
| 2004/0195876 | A1* | 10/2004 | Huiban | A47C 9/002 297/217.3 |
| 2005/0091817 | A1* | 5/2005 | Eger | A47C 31/126 29/407.07 |
| 2005/0209049 | A1* | 9/2005 | Shields | A61H 1/001 482/8 |
| 2006/0226289 | A1* | 10/2006 | Robbins | B60N 2/501 244/122 R |
| 2008/0242521 | A1* | 10/2008 | Einav | A61B 5/1116 482/110 |
| 2009/0058661 | A1* | 3/2009 | Gleckler | A61B 5/103 340/573.7 |
| 2009/0273213 | A1* | 11/2009 | Mukherjee | A47C 31/126 297/217.3 |
| 2011/0269601 | A1* | 11/2011 | Nelson | A47C 7/021 482/8 |
| 2011/0275939 | A1* | 11/2011 | Walsh | A61B 5/4561 600/473 |
| 2012/0184410 | A1* | 7/2012 | Foster | A63B 21/023 482/8 |
| 2013/0011819 | A1* | 1/2013 | Horseman | A61B 5/6887 434/257 |
| 2013/0012786 | A1* | 1/2013 | Horseman | G06F 19/3418 600/301 |
| 2013/0313871 | A1* | 11/2013 | Shalaby | A47C 31/126 297/217.2 |
| 2015/0015399 | A1* | 1/2015 | Gleckler | A61B 5/1116 340/573.7 |
| 2015/0142381 | A1* | 5/2015 | Fitzsimmons | A47C 7/006 702/166 |
| 2015/0351692 | A1* | 12/2015 | Pereny | A61B 5/486 297/217.3 |
| 2015/0352990 | A1* | 12/2015 | Zouzal | A47C 4/54 297/284.3 |
| 2016/0184634 | A1* | 6/2016 | Yanev | A63B 24/0062 482/8 |

* cited by examiner

|  | MODE A (STATIC/ ISOMETRIC) | MODE B (DYNAMIC / AUXOTONIC) |
|---|---|---|
| RESISTANCE SETTING 1 | LUT_A1 | LUT_B1 |
| RESISTANCE SETTING 2 | LUT_A2 | LUT_B2 |
| RESISTANCE SETTING 3 | LUT_A3 | LUT_B3 |

ACTIVE FITNESS CHAIR APPLICATION

This application claims priority from U.S. Provisional Application No. 62/162,317, title DYNAMIC WELLNESS CHAIR and filed 15 May 2015. This application is hereby incorporated by reference in its entirety for all purposes. This application claims priority from U.S. Provisional Application No. 62/336,722, titled ACTIVE FITNESS CHAIR APPLICATION and filed 15 May 2016. This application is hereby incorporated by reference in its entirety for all purposes.

BACKGROUND

1. Field

This application relates generally to exercise devices and more specifically to a system, article of manufacture and method for an active fitness chair application.

2. Related Art

Increasing, workers are employed in jobs that requite a lot of sitting. Sitting an lead to various health issues such as muscle weakness, back pain, weight gain, and the like. Workers may not be motivated to exercise and/or perform other activities that counteract the negative effects of sedentary sitting. Accordingly, a dynamic exercise chair can transform sitting into an active activity and improve the health of the worker.

BRIEF SUMMARY OF THE INVENTION

In one aspect, a computerized-method includes the step of provides a dynamic exercise chair. The dynamic exercise chair includes one or more force providing elements that provide a resistance force to a seatback of the dynamic exercise chair. The dynamic exercise chair includes one or more position sensors, wherein a position sensor monitors a seatback position of the dynamic exercise chair. The dynamic exercise chair includes a seatback position resistance system that provides a resistance force to the seatback of the dynamic exercise chair. The dynamic exercise chair includes a microcomputer system that provides a set of control signals to the one or more force providing elements, and receives a sensor data from the one or more position sensor sensors. The microcomputer system includes a computer networking interface that communicates a set of information one or more force providing elements and a set of information about the one or more position sensor sensors to a mobile device application server that manages a mobile-device application in a mobile device of a user. The computerized-method obtains a historical set of resistance force information from the dynamic exercise chair for a specified period of time. The computerized-method obtains a historical set of position sensor from the dynamic exercise chair for a specified period of time. The computerized-method renders a user interface image that includes the set of historical set of resistance information and the historical set of position sensor. The computerized-method communicates the user interface image to the dynamic exercise chair application in a user's mobile device for display. Other sensors, such as, inter alia: physiological wellness monitoring sensors that monitor biometric parameters can also be utilized.

Figure 4:

A lookup table that is provided to a mobile-device application is shown in FIG. 4.

Figure 5:
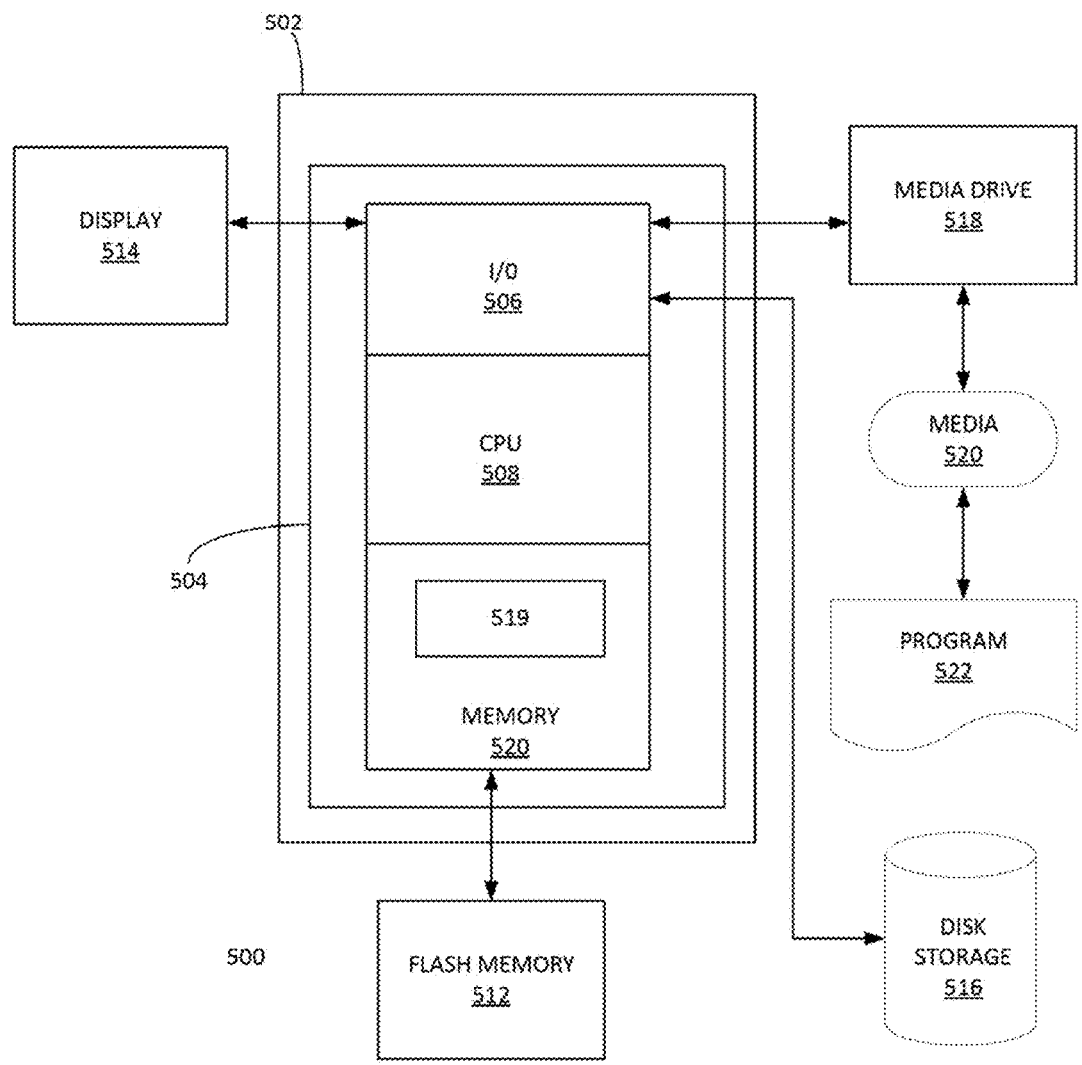

FIG. 5 depicts an exemplary computing system that can be configured to perform any one of the processes provided herein.

Figure 6:
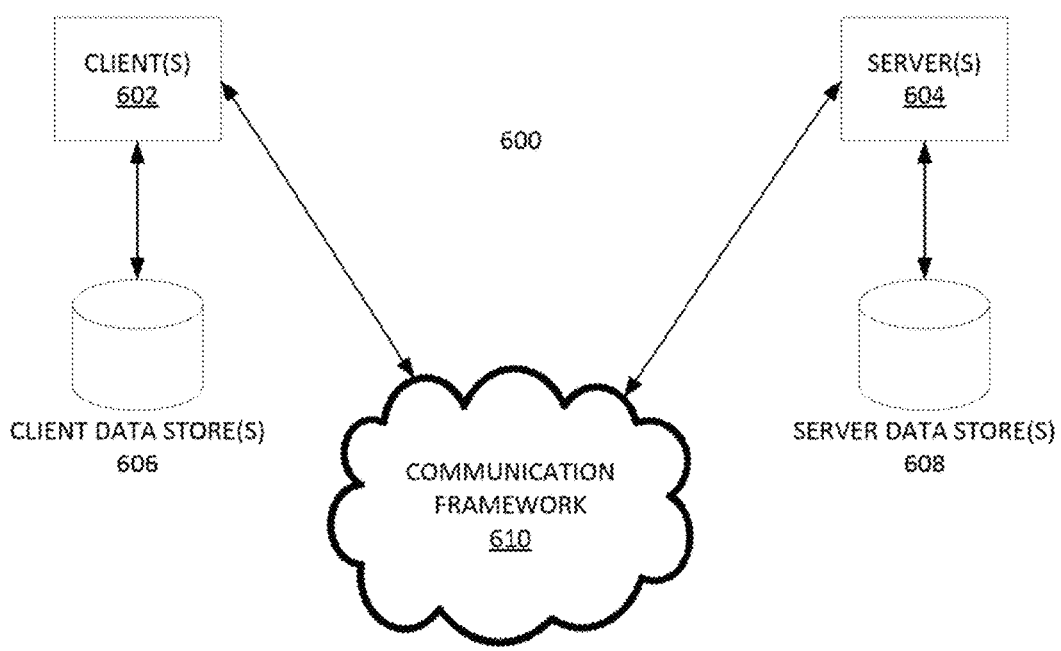

FIG. 6 illustrates another block diagram sample-computing environment with which embodiments may interact.

The Figures described above are a representative set, and are not an exhaustive with respect to embodying the invention.

DESCRIPTION

Disclosed are a system, method, and article of manufacture of an active fitness chair application. The following description is presented to enable a person of ordinary skill in the art to make and use the various embodiments. Descriptions of specific devices, techniques, and applications are provided only as examples. Various modifications to the examples described herein can be readily apparent to those of ordinary skill in the art, and the general principles defined herein may be applied to other examples and applications without departing from the spirit and scope of the various embodiments.

Reference throughout this specification to "one embodiment," "an embodiment," 'one example,' or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following, description, numerous specific details are provided to provide thorough understanding of embodiments of the invention. One skilled in the relevant art can recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flown chart diagrams. As such, the depicted order and labeled steps are indicative of one embodiment of the presented method. Other steps and methods may be conceived, that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, and they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Definitions

Activity trackers can be a wireless-enabled wearable technology device that measure data such as the number of steps walked, heart rate, quality of sleep, steps climbed, and/or other personal metrics.

Actuator can be a type of motor that is responsible for moving or controlling mechanism or system.

Isometric can be a form of resistance exercise in which one's muscles are used in opposition with other muscle groups.

Isometric contraction can occur when the muscle tenses while not changing length. Examples of isometric contraction can include poses in body building and/or pushing against an immoveable object.

Transducer can be a device that converts one form of energy to another form of energy.

Exemplary Architecture

Figure 1:
FIG. 1 illustrates a side view of an embodiment of a dynamic exercise chair, according to some embodiments.

FIG. 1 illustrates a side view of an embodiment of a dynamic exercise chair, according to some embodiments. The dynamic exercise chair 100 can be supported by a caster assembly 101 for mobility, and a locking gas spring assembly 102 for providing height adjustment. The seat support 103 can be rigidly affixed to the top section of the gas spring's shaft. The seat 104 can be pivotably, and/or slidably connected to the seat support. A seatback support 105 can be pivotably connected to the seat support. A seatback carriage can be slidably connected to the seatback support.

The seatback 107 can be rigidly, pivotably about one or ore axis, and/or slidably connected to the seatback carriage. The seatback may traverse a translational path defined by the geometry of the seatback carriage and seatback support. The impetus for the translational motion of the seatback carriage can be provided by frictional force between the user's back and the seatback, or by an explicit mechanical coupling between the pivotably connected members of the seatback support 105 and the seat support 103, or by some combination thereof.

The seatback carriage 106 can be held in a position such that it may translate toward the pivot when the chair is being reclined by the example, to accomplish this, a counterbalance assembly 108 including of one or more springs and one or more stages of pulleys can be used to induce tension in one or more tensile elements 109 such that the tension is sufficient to counteract the force of gravity acting on the seatback 107 and seatback carriage 106 when the seatback support 105 is the upright position.

An adjustment carriage 110 can enable the user to modify the torque and/or force profile exerted by the force providing element(s) 111 to the seatback support about the pivot connecting the seat support to the seatback support. One end of the force providing element(s) can be pivotably connected to the adjustment carriage 10. The adjustment carriage can be slidably connected to the lower portion of the seatback support 105. By moving the adjustment carriage further from the location of the pivot the magnitude of the torque produced at the pivot can be increased. Likewise, by moving the adjustment carriage closer to the pivot the magnitude of the torque produced at the pivot can be reduced. Other linkages may be used to achieve the same motions within the range of interest.

The user can select from resistance modes by means of a selection level 112 or other apparatus to control a selector mechanism 113. The force providing element(s) can be pivotably connected to a component of the selection mechanism, which itself is pivotably connected to the seat support. When the user actuates the selection mechanism, the position of one end of the force providing element(s) 111 end-point can be changed. The selection mechanism can be configured such that one resistance mode. This is also referred to as the static and/or isometric mode herein. The resistance mode can cause the seatback to exert force against the user back. In order to remain in an upright position the user can resist this force utilizing the extensor muscles of the user's lower back.

A sensor system can be included in the selection mechanism such that the selected mode may be queried by a microcomputer (e.g. see infra). Another resistance mode can be the dynamic mode. In this mode the user can exert a force against the seatback 107 in order to recline the e back support 105 about the pivot. In doing so, the user a exercise the extensor muscles (and/or core muscles and/or pelvic muscles) of the longer back throughout the range of the reclining motion.

A microcomputer system (e.g. see FIG. 5 infra) can be included for monitoring the user's sitting and/or exercising activities. The microcomputer system can include various network systems (e.g. Wi-Fi, Bluetooth®, etc.) for communicating feedback to computing system that can then organize and/or display the feedback to the user. When the chair is in the static/isometric; mode, the user may be alerted via an output device. Example output devices, include inter alia: a vibratory transducer. The output device can alert the user when the seatback is outside a nominal ergonomic range. The status of the chair is provided to the microcomputer via the one or more sensors. One or more of the sensors may monitor the angular position of the seatback support 105 relative to the seat support 103. These sensors can be positional sensors such as, inter alia: a rotary encoder, a potentiometer, an accelerometer, an angular rate sensor, and/or etc.

Additional sensors can monitor the positions of the seatback carriage 106, the adjustment carriage 109, the selection mechanism 113, and can also directly measure the forces being applied to the seatback 107 or seat 104, and can also monitor other aspects of the user's sitting and/or exercise. Such sensors can include devices that monitor physical parameters of the chair and user, and/or devices that monitor biometric parameters of the user. Such sensors can include direct force and/or shear sensing, linear and/or angular position and/or velocity and/or acceleration sensing, temperature sensing, heart rate sensing, muscle activation sensing, and/or other physical and biometric sensors known in the art. This data can be processed either onboard the microcomputer or by another device with a data connection to the microcomputer. Such data can be used to provide the user with short-duration feedback, or example vibrating a transducer to remind the user t use the chairs exercise functions. It can also be used to provide to the user raw or summarized data of the user's longer-duration progress. To communicate such feedback to the user, the embodiment can include transducers and/or displays that engage any of the sensory modalities such as audio transducers, visual displays, electrocutaneous stimulators, olfactory emitters, and/ or any other means known the art.

The embodiment can also include actuators and/or transducers with the means to adjust some physical parameter of the device. Such actuators can be used to adjust, for example, the position of the adjustment carriage via a leadscrew actuator, the torque acting upon the pivot via an electromechanical brake. Such actuators can operate independently of or in conjunction with the user feedback system.

The chair also includes an adjustable footrest assembly 114 which can assist the user in performing the exercises by positioning the user's feet appropriately and consistently. The chair also can have a pair of armrests that can also have exercise functionality. The chair can also have a headrest, which can also have exercise functionality.

It is noted that various other resistance systems can be integrated with dynamic exercise chair 100. This include resistance systems for exercising a user's arms, hands, legs, feet and/or neck. Various sensors such as pulse sensors, respiratory rate sensors, galvanic skin response sensors, etc. These systems and/or sensors can be monitored and an overall physiological state of the user can be calculated. This data can be presented to a user via a mobile-device application interface. The sensor data of dynamic exercise chair 100 can also be integrated with that of other physiological monitoring devices worn by the user (e.g. an activity tracker, biomedical sensors, etc.).

Example Processes

Figure 2:
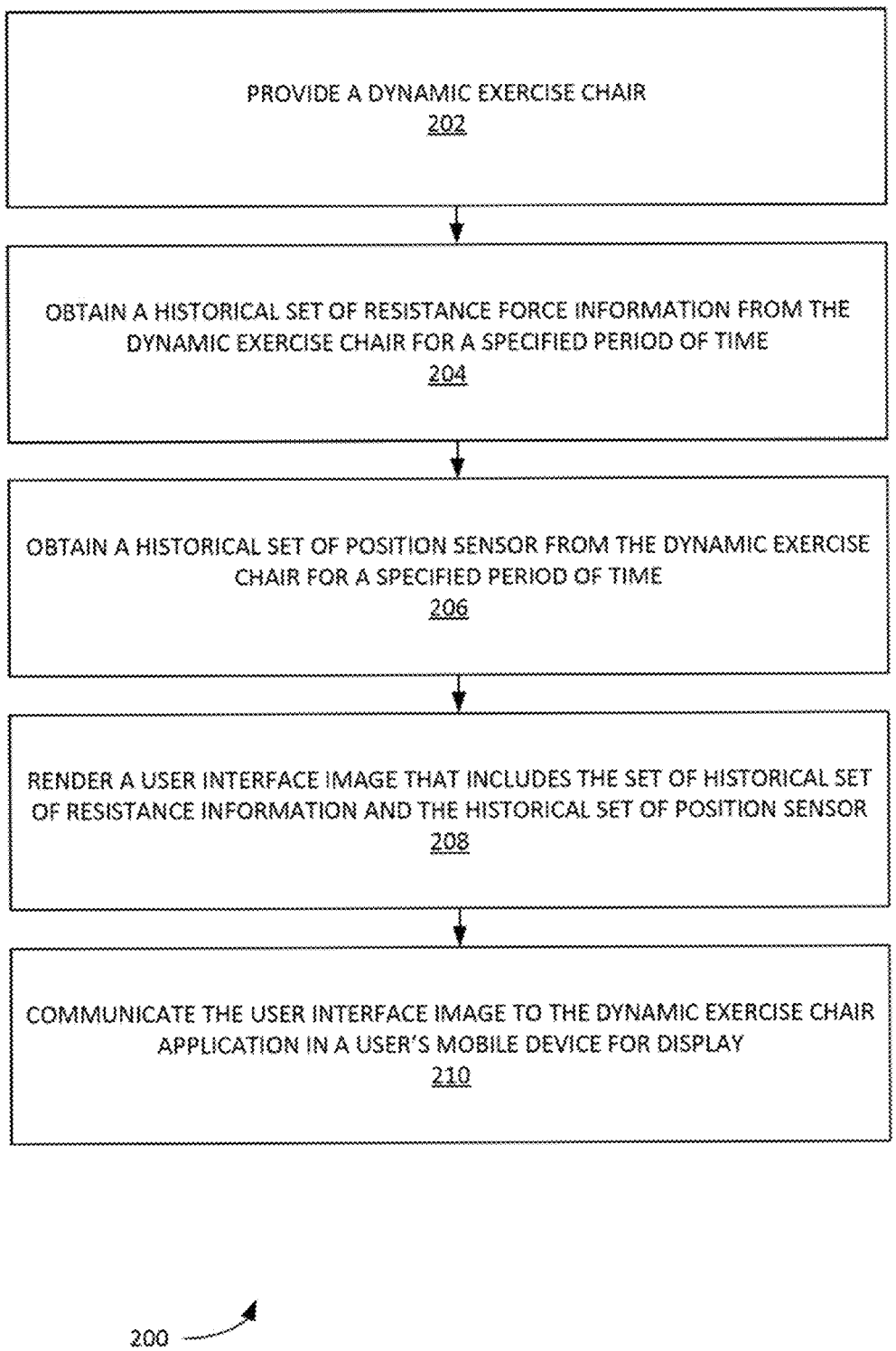
FIG. 2 illustrates an example process for a dynamic exercise chair application, according to some embodiments.

FIG. 2 illustrates are example process 200 for a dynamic exercise chair application, according to some embodiments. In step 202, process 200 can provide a dynamic exercise chair. The dynamic exercise chair can include one or more force providing elements that provide a resistance force to a seatback of the dynamic exercise chair. The dynamic exercise chair can include one or more position sensors. A position sensor monitors a seatback position of the dynamic exercise chair. The dynamic exercise chair can include a seatback position resistance systems that provides a resistance force to the seatback of the dynamic exercise chair. The dynamic exercise chair an include microcomputer system that provides a set of control signals to the one more force providing elements, and receives a sensor data from the one or more position sensor sensors. The microcomputer system comprises a computer networking interface that communicates a set of information one or more force providing elements and a set of information about the one or more position sensor sensors to a mobile device application server that manages a mobile-device application in a mobile device of a user. In step 204, process 200 can obtain a historical set of resistance force information from the dynamic exercise chair for a specified period of time. In step 206, process 200 obtain a historical set of position sensor from the dynamic exercise chair for a specified period of time. In step 208, process 200 can render a user interface image that includes the set of historical set of resistance information and the historical set of position sensor. In step 210, process 200 can communicate the user interface image to the dynamic exercise chair application in user's mobile device for display. The mobile device can display the user interface image.

Figure 3:
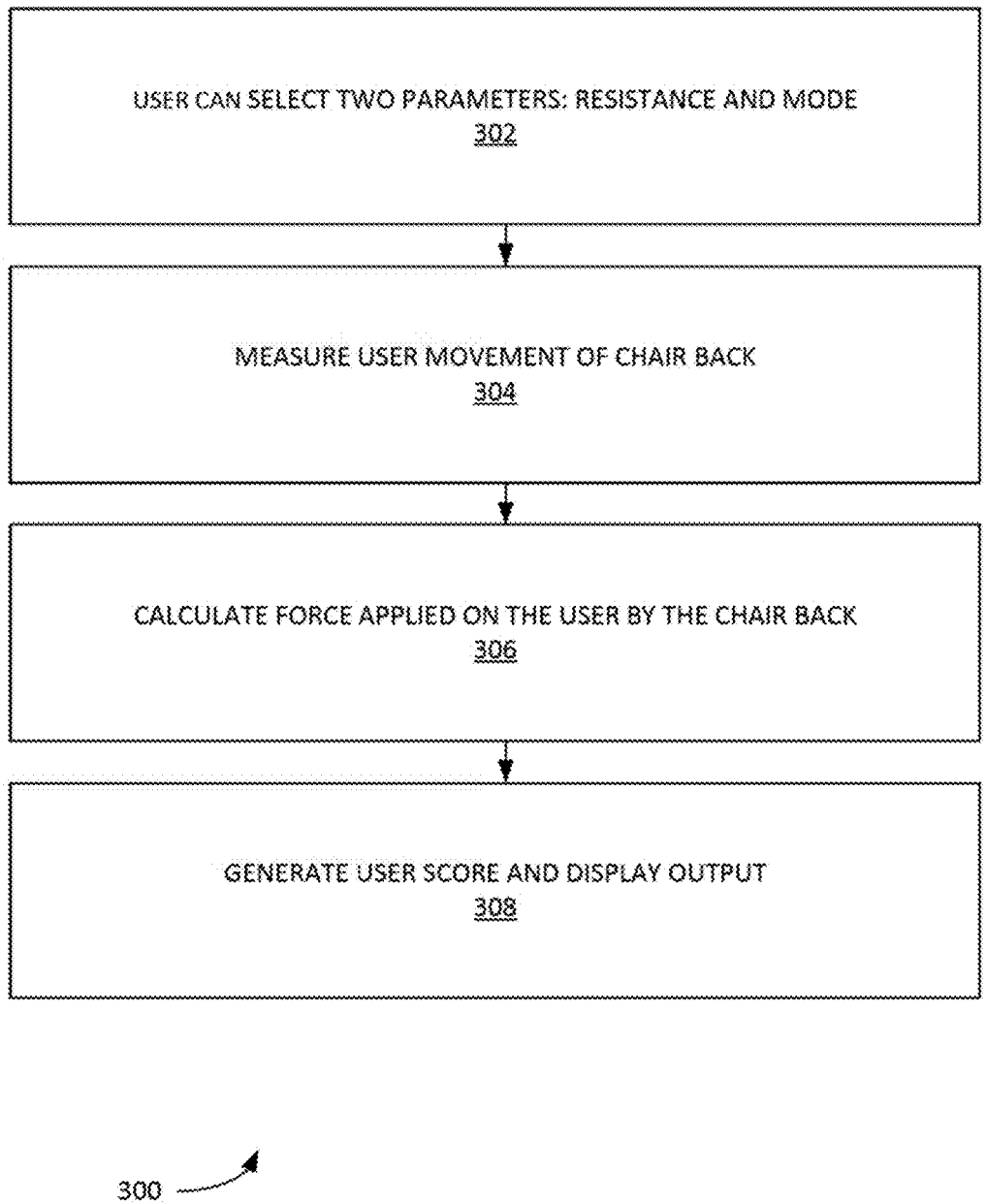
FIG. 3 illustrates an example process for assign a user a score that reflects the cumulative amount of beneficial exercise performed in a given time period, according to some embodiments.

FIG. 3 illustrates an example process 300 for assign a user score that reflects the cumulative amount of beneficial exercise performed in a given time period, according to some embodiments. In step 302 of process 300, a user a select two parameters: resistance and mode. Each combination of resistance and mode settings corresponds to a lookup table (LUT). This lookup table will be provided to the application as some sort of delimited text file, and can be exogenous to the application so that changes can be made as necessary. For example, if there are two modes and three resistance settings, there would be six lookup tables (LUT) 400 that would be provided to the application as provided in FIG. 4.

In step 304, user movement of the chair back can be detected and measured. In step 306, the force of the user on the chair back can be calculated. The force can be represented as a score. For example, an application can use a lookup table to query an angular position, $\theta$, and retrieve an estimate of the force being applied to the user's back at that position, as well as a score factor for that position. The score factor can take into account both the estimated force and weights it according to how difficult it is for the user to exert a force as that particular position. In step 308, user score can be generated and displayed as output. The data produced by process 300 can be stored in a database. The data produced by process 300 can be communicated to a health-care provider for analysis and/or integrated into a user's health tracker and/or activity tracker profile.

Example Computer Systems

FIG. 5 depicts an exemplary computing system 500 that can be configured to perform any one of the processes provided herein. In this context, computing system 500 may include, for example, processor, memory, storage, and I/O devices (e.g., monitor, keyboard, disk drive, Internet connection, etc.). However, computing system 500 may include circuitry or other specialized hardware for carrying out some or all aspects of the processes. In some operational settings, computing system 500 may be configured as a system that includes one or more units, each of which is configured to carry out some aspects of the processes either in software, hardware, or some combination thereof.

FIG. 5 depicts computing system 500 with a number of components that may be used to perform any of the processes described herein. The main system 502 includes a motherboard 504 having an I/O section 506, one or more central processing units (CPU) 508, and a memory section 510, which may have a flash memory card 512 related to it. The I/O section 506 can be connected to a display 514, a keyboard and/or other user input (not shown), a disk storage unit 516, and a media drive unit 515. The media drive unit 518 can read/write a computer-readable medium 520, which can contain programs 522 and/or data. Computing system 500 can include a web browser. Moreover, is noted that computing system 500 can be configured to include additional systems in order to fulfill various functionalities. Computing system 500 can communicate with other computing devices based on various computer communication protocols such a Wi-Fi, Bluetooth® (and/or other standards for exchanging data over short distances includes those using short-wavelength radio transmissions), USB, Ethernet, cellular, an ultrasonic local area communication protocol, etc. Dynamic exercise chair application 519 can be used to display dynamic exercise chair information, manage dynamic exercise chair modes, register users, and the like.

FIG. 6 illustrates another block diagram of a sample computing environment 600 with which embodiments may interact. The system 600 further illustrates a system that includes one or more clients 602. The client(s) 602 may be hardware and/or software (e.g., threads, processes, computing devices). The system 600 also includes one or more servers 604. The server(s) 604 may also be hardware and/or software (e.g., threads, processes, computing devices). One possible communication between a client 602 and a server 604 may be in the form of a data packet adapted to be transmitted between two or more computer processes. The system 600 includes a communication framework 610 that may be employed to facilitate communications between the client(s) 602 and the server(s) 604. The client(s) 502 are connected to one or more client data stores 606 that may be employed to store information local to the client(s) 602.

Similarly, the server(s) 604 are connected to one or more server data stores 608 that may be employed to store information local to the server(s) 604.

The systems of FIGS. 1, 5-6 can be used to implement the computerized systems, models and/or processes of FIGS. 3-4 and/or other methods provided herein, according to various embodiments. The systems of FIGS. 1-6 can be used to implement the use cases discussed infra. It is further noted that the data gathered by the systems of FIGS. 1-6 can gathered and/or synchronized with other personal wearable/embeddable/fitness trackers in order to optimize/incentivize personal fitness.

Exemplary Use Cases

In some examples, a dynamic wellness chair (e.g. an active fitness chair) device employs two optional resistance functions. The static (or isometric) mode can allow 'active sitting' where muscles are volitionally engaged as the user resists a selectable force being applied by the seatback in order to maintain a static, upright sitting position. The dynamic mode can allow the user to perform a repetitive reclining exercise by overcoming a resistive force. The resistance profile an be selectable by the user depending on the user's degree of fitness and the desired fitness outcome. The design can allow for an exaggerated angle of recline. When in a reclined position the chair supports a greater component of the user's upper torso, minimizing compressive forces in the spinal elements. An embedded feedback system, comprised of embedded sensors and transducers linked to an embedded microcomputer, tracks the chair's positioning, helping the user to maintain a healthy posture while sitting. This may be achieved by signaling the user when the chair detects that the user's posture has deviated from the optimal range. The feedback system may also remind the user to perform exercises based on a personalized interval schedule. Personalized metrics can be provided to the use by measuring the user's sitting habits and exercising activity. Such metrics may be useful to motivate the user's therapeutic use of the device by providing the user with achievable fitness objectives. The data may be collected, compared and compiled allowing an improvement in the personal sitting habits.

CONCLUSION

Although the present embodiments have been described with reference to specific example embodiments, various modifications and changes can be made to these embodiments without departing from the broader spirit and scope of the various embodiments. For example, the various devices, modules, etc. described herein can be enabled and operated using hardware circuitry, firmware, software or any combination of hardware, firmware, and software (e.g., embodied in a machine-readable medium).

In addition, it can be appreciated that the various operations, processes, and methods disclosed herein can be embodied in a machine-readable medium and/or a machine accessible medium compatible with a data processing system (e.g., a computer system), and can be performed in any order (e.g., including using means for achieving the various operations). Accordingly, the specification and drawings are to be regarded in an illustrative rather than a restrictive sense. In some embodiments, the machine-readable medium can be a non-transitory form machine-readable medium.

What is claimed:

1. A computerized method for a dynamic exercise chair system, the computerized method comprising:

providing a dynamic exercise chair, wherein the dynamic exercise chair comprises:

a plurality of force providing elements in a seatback carriage, wherein the plurality of force providing elements provide a resistance force modifiable to a seatback of the dynamic exercise chair, wherein the seatback carriage is slidably connected to a seatback support of the dynamic exercise chair, and wherein the seatback may traverse a translational path defined by geometry of the seatback carriage and the seatback support;

a plurality of position sensors, wherein a position sensor monitors a seatback position of the dynamic exercise chair;

and a microcomputer system that provides a set of control signals to the plurality of force providing elements, and receives a sensor data from the plurality of position sensors, and wherein the microcomputer system comprises a computer networking interface that communicates a set of information about the plurality of force providing elements and a set of information about the plurality of position sensors to a mobile device application server that manages a mobile-device application in a mobile device of a user;

and wherein the microcomputer system is configured to:

obtain a historical set of resistance force information from the dynamic exercise chair for a specified period of time;

obtain a historical set of position sensor information from the dynamic exercise chair for the specified period of time;

render a user interface image that includes the historical set of resistance force information and the historical set of position sensor information;

communicate the user interface image to the mobile-device application in the user's mobile device for display; and cause the plurality of force providing elements to enter a dynamic force mode that provides a dynamic user-selected resistance force to the seatback of the dynamic exercise chair on a user-specified periodicity of a repetitive reclining exercise performed by the user, wherein the resistance force is capable of being selected by the user, and wherein a seatback resistance characteristic comprises a dynamic resistance of a specified dynamic force.

2. The computerized method of claim 1 further comprising a dynamic exercise chair seat sensor configured to sense when a user sits in the dynamic exercise chair, and wherein the specified period of time initiates upon sensing that the user is sitting.

3. The computerized method of claim 2, wherein the microcomputer system is configured to receive the seatback resistance characteristic and resistance force preferences from the mobile-device application as selected by the user.

4. The computerized method of claim 3, wherein the microcomputer system is configured to cause the dynamic exercise chair to enter an isometric exercise mode, and wherein the seated resistance characteristic comprises an isometric resistance of a specified isometric force configured to be provided at a user specified seatback position.

5. The computerized method of claim 3, wherein the microcomputer system is configured to cause the plurality of force providing elements to alternate between an isometric force mode and the dynamic force mode at a specified interval while the user is sitting in the dynamic exercise chair.

6. The computerized method of claim 5, wherein the microcomputer system is configured to detect a user activity while the user is sitting in the dynamic exercise chair, wherein the dynamic exercise chair is determined to be in the isometric force mode, and wherein the microcomputer system is configured to cause the dynamic exercise chair to switch to the dynamic force mode when the user activity is detected.

7. The computerized method of claim 6, wherein the microcomputer system is configured to detect that the user activity has terminated while the user is sitting in the dynamic exercise chair, and wherein the microcomputer system is configured to cause the dynamic exercise chair to switch to the isometric force mode.

8. The computerized method of claim 7, wherein the dynamic exercise chair comprises a vibratory transducer controlled by the microcomputer system, wherein the microcomputer system is configured to detect that the seatback is outside a nominal ergonomic range, and wherein the microcomputer system is configured to cause the vibratory transducer to vibrate to alert the user that the seatback is outside the nominal ergonomic range.

9. The computerized method of claim 8, wherein the microcomputer system is configured to count a number of recline repetitions of the repetitive reclining exercise performed by the user and includes the number of recline repetitions in the historical set of resistance information.

10. The computerized method of claim 9, wherein the user activity is a telephone conversation with the mobile device that comprises the mobile-device application.

11. A computerized system of an active fitness exercise chair system, the computerized system comprising:
   a plurality of force providing elements in a seatback carriage, wherein the plurality of force providing elements provide a resistance force to a seatback of the active fitness exercise chair system, wherein the seatback carriage is slidably connected to a seatback support of the active fitness exercise chair system, and wherein the seatback may traverse a translational path defined by geometry of the seatback carriage and the seatback support
   a plurality of position sensors, wherein a position sensor monitors a seatback position of the active fitness exercise chair system;
   a microcomputer system that provides a set of control signals to the plurality of force providing elements, and receives a sensor data from the plurality of position sensors, and wherein the microcomputer system comprises a computer networking interface that communicates a set of information about the plurality of force providing elements and a set of information about the plurality of position sensors to a mobile device application server that manages a mobile-device application in a mobile device of a user;
   a processor configured to execute instructions;
   a memory containing instructions, the instructions, when executed on the processor, cause the processor to perform operations that:
   obtain a historical set of resistance force information from the active fitness exercise chair system for a specified period of time;
   obtain a historical set of position sensor information from the active fitness exercise chair system for the specified period of time;
   render a user interface image that includes the historical resistance force information and the historical set of position sensor information; and
   communicate the user interface image to the mobile-device application in the user's mobile device for display; and
   cause the plurality of force providing elements to enter a dynamic force mode that provides a dynamic user-selected resistance force to the seatback of the active fitness exercise chair system on a user-specified periodicity of a repetitive reclining exercise performed by the user, wherein the resistance force is capable of being selected by the user, and wherein a seatback resistance characteristic comprises a dynamic resistance of a specified dynamic force.

12. The computerized system of claim 11, wherein the microcomputer system is configured to receive the seatback resistance characteristic and resistance force preferences from the mobile-device application as selected by the user.

13. The computerized system of claim 12, wherein the microcomputer system causes the active fitness exercise chair system to enter an isometric exercise mode, and wherein the seatback resistance characteristic comprises an isometric resistance of a specified isometric force configured to be provided at a user specified seatback position.

14. The computerized system of claim 13, wherein the active fitness exercise chair system includes a physiological monitoring system, and wherein the microcomputer system is configured to determine a positioning of the active fitness exercise chair system in a room and facilitate a return of the active fitness exercise chair system to a preprogrammed position at a desk in the room using a plurality of electromagnetic mechanisms.

* * * * *